United States Patent [19]

Stephenson

[11] Patent Number: 4,526,172

[45] Date of Patent: Jul. 2, 1985

[54] ONE PIECE MULTI-PURPOSE CLAMP

[75] Inventor: Stanley Stephenson, Huntington Beach, Calif.

[73] Assignee: Premium Plastics, Inc., Chicago, Ill.

[21] Appl. No.: 526,448

[22] Filed: Aug. 25, 1983

[51] Int. Cl.³ .............................................. A61B 17/28
[52] U.S. Cl. .................................. 128/322; 128/325; 128/346; 81/338
[58] Field of Search ............... 128/346, 321, 322, 325; 251/10; 81/425 A, 425 R, 426, 428 R; 269/257, 6; 294/118, 119; 604/338, 340

[56] References Cited

U.S. PATENT DOCUMENTS

| 643,003 | 2/1900 | Pollock | 128/346 |
|---|---|---|---|
| 1,359,164 | 11/1920 | Lo Giudice . | |
| 2,109,147 | 2/1938 | Grosso . | |
| 2,653,844 | 9/1953 | Detwiler | 81/426 X |
| 2,962,024 | 11/1960 | Raymond . | |
| 3,604,071 | 7/1969 | Reimels | 128/346 X |
| 3,777,760 | 12/1973 | Essner . | |
| 3,906,957 | 9/1975 | Weston . | |
| 4,120,302 | 10/1978 | Ziegler . | |
| 4,212,305 | 7/1980 | Lahay | 128/354 |

FOREIGN PATENT DOCUMENTS 2821893 12/1978 Fed. Rep. of Germany ...... 128/321

Primary Examiner—Michael H. Thaler
Attorney, Agent, or Firm—Dressler, Goldsmith, Shore, Sutker & Milnamow, Ltd.

[57] ABSTRACT

A unitary, one-piece multi-purpose plastic clamp is disclosed which is adaptable for a wide variety of uses. The clamp includes a pair of pivotally interconnected pincer portions, and a pair of pivotally interconnected handle portions, with the pincer portions further respectively pivotally connected to the handle portions. Movement of finger grips defined by the handle portions toward each other creates a clamping force between the respective clamping surfaces of the pincer portions. In order to maintain the clamp in a closed, clamping condition, first and second locking structures are respectively provided on the handle portions of the clamp. The first and second locking structures respectively preferably comprise at least one first locking tooth and at least one second locking tooth which releasably engage each other, and which are selectively disengagable by relative disengaging movement of the handle portions of the clamp. The clamp includes structure for resisting relative disengaging movement of the handle portions, thereby avoiding inadvertent or accidental release of the clamp.

12 Claims, 7 Drawing Figures

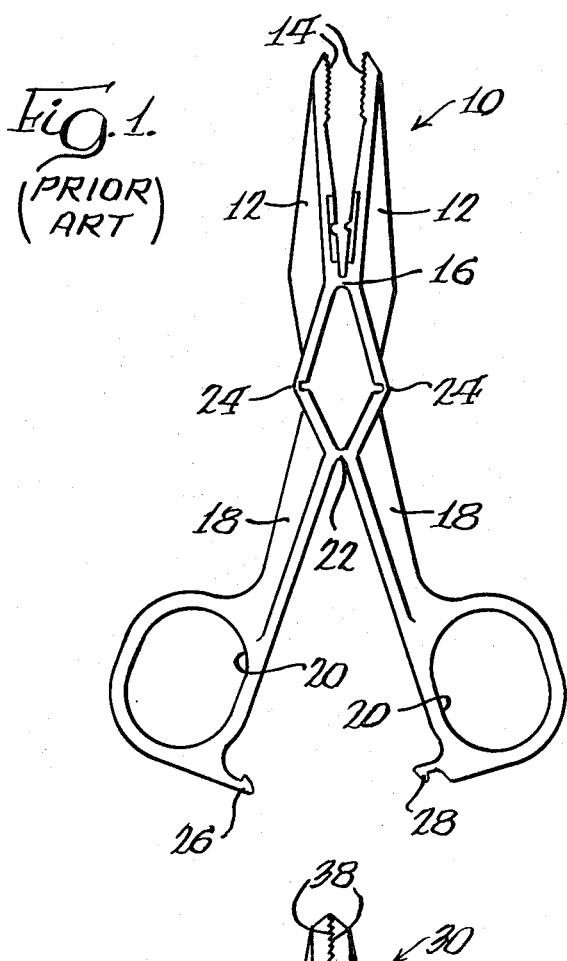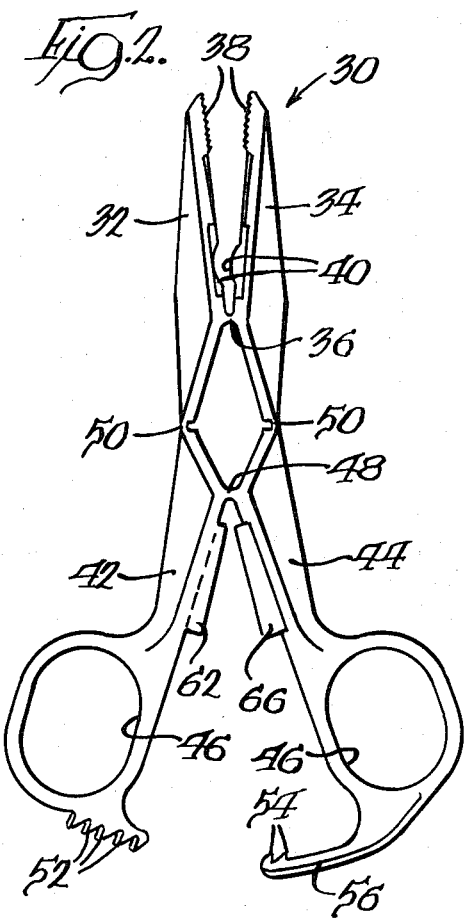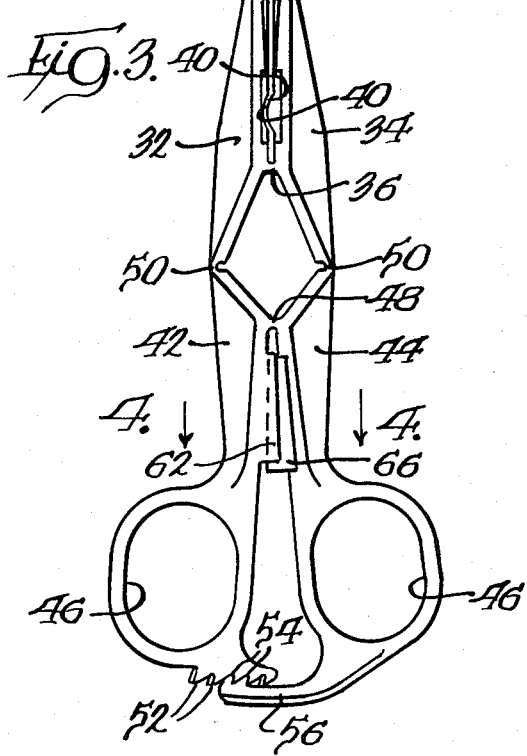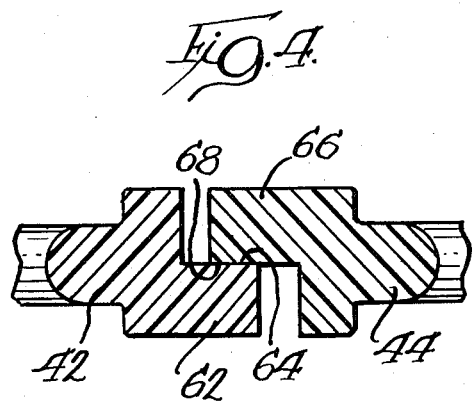

ONE PIECE MULTI-PURPOSE CLAMP

TECHNICAL FIELD

The present invention relates generally to manually-operable clamps and the like, and more particularly to a one-piece plastic clamp having mutually engageable first and second locking means which are disengageable by relative disengaging movement of the handle portions of the clamp, and which includes means for resisting relative disengaging movement of the handle portions.

BACKGROUND OF THE INVENTION

Various constructions are known for forceps, hemostats, and like manually operable clamps which have a generally scissors-like working action. Clamps of this description are widely used for many different purposes in the health care industry and also find wide application in areas apart from medically-related uses. Frequently, such clamps include selectively operable locking means for maintaining the clamping force created by the clamp, such as for clamping of a rubber tube to maintain the tube in a closed or constricted condition.

While in the past many of the above-described clamps have been fabricated from suitably corrosion-resistant metallic materials, clamps of such construction are relatively expensive. Because of the highly versatile nature of such clamps, efforts have been more recently made to perfect a relatively inexpensive clamp made of plastic materials. By providing a selectively lockable clamp which is relatively inexpensive, such a clamp becomes practical for use in not only many health care-related applications, but also for use such as in manufacturing operations, hobby activities, or whereever else a selectively and easily applicable clamping force can be advantageously employed.

One previous plastic clamp which has been developed is of unitary plastic construction, including a pair of pivotally interconnected pincer portions, and a pair of pivotally interconnected handle portions. One end of each pincer portion is pivotally connected to one end of a respective one of the handle portions, with all of the pivotal connections of the clamp provided by integral "living" hinges. This previous clamp further includes a pair of cooperating locking teeth respectively provided on the handle portions of the clamp. The locking teeth are engagable generally be movement of the handle portions toward each other, which in turn causes the respective ends of the pincer portions to move together for clamping. Disengagement of the locking teeth for release of the clamp is effected by relative disengaging movement of the handle portions transversely of a plane which extends through the pincer and handle portions of the clamp.

One serious problem encountered with the use of the above-described plastic clamp is the relative ease with which the locking teeth of the clamp can be disengaged. Primarily due to the inherent flexibility of the plastic material from which such a clamp is fabricated, relatively little force is required to relatively move the handle portions of the clamp for disengaging its locking teeth. Consequently, a relatively slight disturbance of the clamp can result in its inadvertent release. At best, such inadvertent release of the clamp is inconvenient, while at worst (particularly in medically-related applications) inadvertent release of the clamp can be potentially serious.

Accordingly, a very real need exists for an easily-operable, relatively inexpensive one-piece plastic clamp which can be selectively maintained in a closed or clamping condition, and which is configured to resist inadvertent or accidental release.

SUMMARY OF THE INVENTION

A one-piece, multi-purpose unitary plastic clamp is disclosed embodying the principles of the present invention. The preferred fabrication of the clamp from plastic material permits it to be relatively inexpensively manufactured, thus permitting the clamp to be economically employed for many different applications. Notably, the manually-operable handle portions of the clamp are respectively provided with mutually engagable locking means which can be selectively engaged for maintaining a clamping force on an associated article, with the clamp further including means for resisting relative movement of the handle portions for disengaging the respective locking means.

In the illustrated embodiment, the present one-piece plastic clamp includes a pair of pincer portions each having first and second ends, and each having a respective clamping surface at one end thereof. The clamp further includes a pair of handle portions each defining a finger grip adapted for manipulation by hand.

Means are provided for interconnecting the pincer portions and the handle portions whereby movement of the finger grips of the handle portions toward each other in a plane extending through the pincer and handle portions moves the clamping surfaces of the pincer portions toward each other for creating a clamping force therebetween. In the preferred embodiment, the interconnecting means comprise a plurality of integral, "living" hinges. Specifically, the pair of pincer portions are pivotally connected to each other intermediate the respective ends thereof by a living hinge. Similarly, the pair of handle portions are pivotally connected to each other intermediate the respective ends thereof by another living hinge. A pair of living hinges are provided for respectively pivotally connecting the second end of each of the pincer portions with one of the ends of a respective one of the handle portions. The living hinges generally define hinging axes which are parallel to each other and extend generally perpendicular to the plane which extends through the pincer and handle portions of the clamp. By this construction, movement of the finger grips of the handle portions toward each other correspondingly moves the clamping surfaces of the pincer portions toward each other for creating a clamping force between the clamping surfaces.

In the preferred embodiment, the clamping surface of each pincer portion at one end thereof comprises a first clamping surface, with each pincer portion further including a second clamping surface disposed between its respective first clamping surface and the living hinge which pivotally connects the pincer portions. These second clamping surfaces, between which a clamping force is created attendant to movement of the finger grips of the handle portions toward each other, are preferably of complementary arcuate configuration to facilitate clamping and closing of a flexible tube therebetween.

In order to permit the clamp to be selectively maintained in a closed condition to maintain the clamping force between the clamping surfaces of the pincer portions, first and second locking means are respectively provided on the handle portions of the clamp. The first and second locking means are adapted to releasably interengage and coact with each other when the finger grips of the handle portions are moved toward each other in the plane which extends through the clamp. Disengagement of the first and second locking means is effected by relative disengaging movement of the handle portions generally transversely of the aforesaid plane in either of opposite directions.

The first locking means preferably comprises one or more locking teeth which extend generally transversely of the plane extending through the clamp. Similarly, the second locking means preferably comprises one or more second locking teeth extending generally transversely of the plane. The one or more second locking teeth are adapted to releasably engage and coact with the one or more first locking teeth for maintaining a clamping force between the clamping surfaces of the pincer portions. A plurality of locking teeth are preferably provided on one of the handle portions of the clamp, with at least one locking tooth provided on the other of the handle portions which is adapted to selectively releasably interengage each locking tooth on the one handle portion for selectively varying and maintaining the clamping force created.

Significantly, the present clamp is configured to resist inadvertent or accidental release, and accordingly includes means for resisting relative disengaging movement of the handle portions of the clamp. In the preferred embodiment, the disengagment resisting means comprises an offset portion which forms a part of each of the first and second locking teeth of the clamp, with the respective offset portions being engagable with each other when the first and second locking teeth are engaged to resist relative disengaging movement of the clamp handle portions in a first direction with respect to the plane extending through the clamp.

In the preferred embodiment, the disengagement resisting means further includes a pair of abutment projections respectively provided on and extending inwardly of the handle portions of the clamp. Each abutment projection defines an abutment surface, with the abutment surfaces being moved into generally confronting relation with each other when the first and second locking means of the clamp are moved into coacting engagement. In this closed condition, the locking surfaces are adapted to engage each other to resist relative disengaging movement of the clamp handle portions in a second direction generally opposite the first direction of disengaging movement.

Thus, the disengagement resisting means of the clamp are preferably configured so that relative disengaging movement of the handle portions is resisted in either direction generally transversely of the plane extending through the clamp. Because of the resilience of the preferred one-piece plastic construction, relative disengaging movement of the handle portions can still be easily effected, but requires a relatively positive manipulation of the handle portions, thus desirably acting to preclude unintentional or accidental release of the clamp.

Numerous other advantages and features of the present invention will become readily apparent from the following detailed description and accompanying drawings.

BRIEF DESCRIPTION OF THE DRAWINGS

FIG. 1 is a plan view of a prior art one-piece plastic clamp;

FIG. 2 is a plan view of an improved one-piece plastic clamp embodying the principles of the present invention, illustrated in an opened or released condition;

FIG. 3 is a plan view of the improved one-piece clamp shown in FIG. 2 illustrating the clamp in a closed condition;

FIG. 4 is a cross-sectional view taken generally along lines 4—4 of FIG. 3;

DETAILED DESCRIPTION

Figure 5:
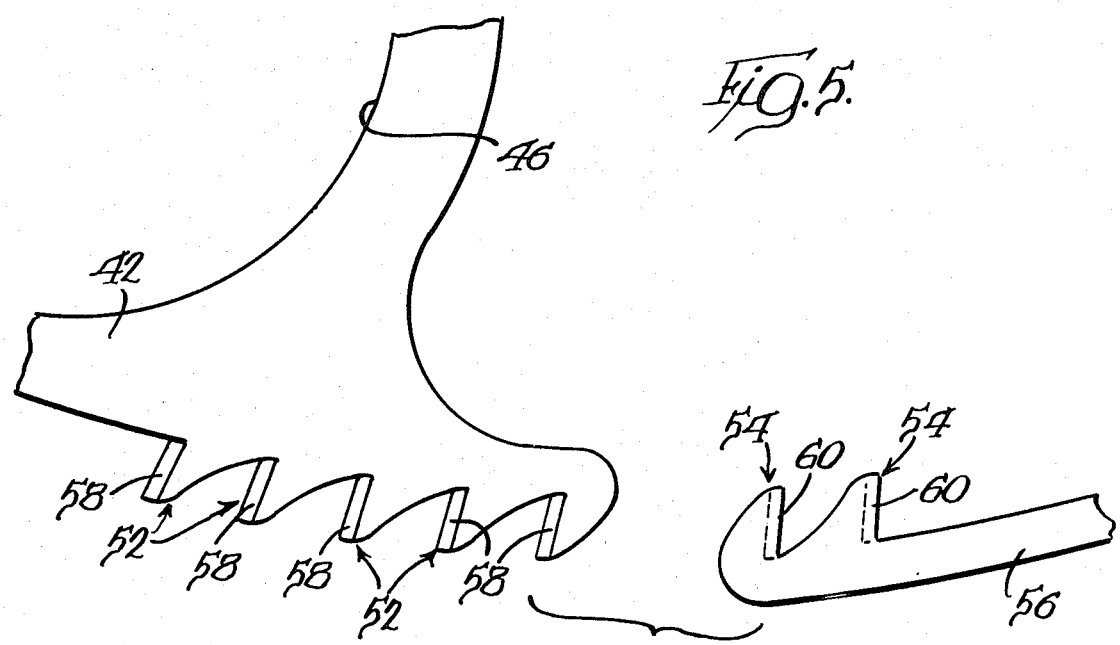
FIG. 5 is an enlarged, fragmentary view illustrating the locking arrangement of the present clamp when the clamp is in its opened condition.

While the present invention is susceptible of embodiment in various forms, there is shown in the drawings and will hereinafter be described a presently preferred embodiment, with the understanding that the present disclosure is to be considered as an exemplification of the invention, and is not intended to limit the specific embodiment illustrated.

FIG. 1 illustrates a one-piece plastic clamp 10 of a previously known construction. The clamp 10 includes a pair of pincer portions 12 each having a clamping surface 14 at respective ends thereof. The pincer portions 12 are pivotally connected to each other for relative hinging movement by a web-like integral living hinge 16 whereby the clamping surfaces 14 are movable toward and away from each other.

The clamp 10 further includes a pair of handle portions 18 which respectively define finger grips 20. The handle portions 18 are pivotally interconnected to each other by a living hinge 22 for relative hinging movement. The pincer portions 12 are respectively pivotally connected to handle portions 18 by a pair of living hinges 24 whereby finger grips 20 can be moved toward each other for moving the clamping surfaces 14 toward each other and for creating a clamping force therebetween.

In order to maintain clamp 10 in a closed condition, a pair of locking teeth 26 and 28 are respectively provided on the handle portion 18. By moving finger grips 20 toward each other, locking teeth 26 and 28 can be moved into releasable, coacting engagement with each other to maintain the clamp in a closed condition.

Release of clamp 10 is effected by relatively moving handle portions 20 transversely of a plane which extends through the handle portions and pincer portions of the clamp. By this action, locking teeth 26 and 28 are disengaged from each other thus permitting the clamp to open. However, the inherent flexibility which results from the plastic construction of clamp 10 results in relatively little force being necessary to relatively move handle portions 20 for disengagement of locking teeth 26 and 28. As a consequence, a relatively slight disturbance of the clamp, such as by inadvertent impact or the like, can undesirably result in unintended release of the clamp.

FIG. 2 illustrates the improved, one-piece plastic clamp 30 embodying the principles of the present invention. Clamp 30 includes a pair of pivotally connected pincer portions 32, 34 each having first and second ends, with the pincer portions being pivotally connected intermediate the respective ends thereof by an integral living hinge 36. In the preferred form, pincer portions 32, 34 respectively include first clamping surfaces 38 at the first ends of the pincer portions, and further respectively include second clamping surfaces 40 disposed between clamping surfaces 38 and living hinge 36. As will be observed, the second clamping surfaces 40 are of complementary, arcuate configuration to facilitate clamping of a flexible tube therebetween for closing or constricting the tube.

Clamp 30 further includes a pair of handle portions 42, 44 which respectively define finger grips 46 adapted for manipulation by hand. The handle portions 42, 44 are pivotally connected to each other intermediate the respective ends thereof by an integral living hinge 48. The second ends of the pincer portions 32, 34 are respectively pivotally connected to one of the ends of the handle portions 42, 44 at integral living hinges 50. It will be noted that the living hinges 36, 48, and 50 define hinging axes which are generally parallel to each other, and which extend generally perpendicularly to a plane extending through the pincer portions 32, 34 and the handle portions 42, 44 of the clamp 30. By this construction, movement of finger grips 46 of handle portions 42, 44 toward each other correspondingly moves clamping surfaces 38 and clamping surfaces 40 together for creating a clamping force between the respective clamping surfaces.

While FIG. 2 illustrates the present clamp 30 in an opened or released condition, it will be appreciated that it is desirable for the clamp to have the capability of being selectively, yet releasably, maintained in a closed and clamping condition, as illustrated in FIG. 3. Accordingly, clamp 30 includes first and second locking means respectively provided on handle portions 42, 44 on ends thereof opposite living hinges 50. The first locking means preferably comprises at least one, and preferably a plurality of first locking teeth 52, which are illustrated as integrally joined to handle portion 42. The second locking means of the clamp 30 preferably comprises at least one second locking tooth 54, with two locking teeth 54 being illustrated as integrally joined to handle portion 44 by a resiliently flexible connector portion 56.

Figure 6:
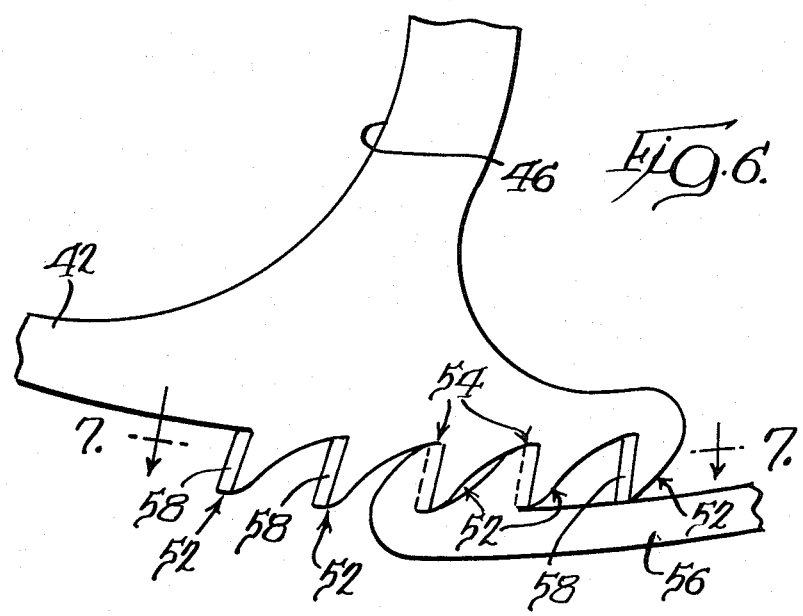
FIG. 6 is an enlarged, fragmentary view similar to FIG. 5 illustrating the locking arrangement of the present clamp when the clamp is in its closed condition.

As best illustrated in FIGS. 5 and 6, first locking teeth 52 and second locking teeth 54 are of generally complementary configuration, with each of the locking teeth extending generally transversely of the plane extending through pincer portions and handle portions of the clamp 30. Interengagement of one or more of second locking teeth 54 with one or more of first locking teeth 52 is easily effected by moving the finger grips 46 of handle portions 42, 44 toward each other so that the teeth of the respective locking means resiliently "ride up" each other and fit into intermeshing, interlocking mutual engagement with each other. In this regard, the resilience of connector portion 56 facilitates resilient movement of the second locking teeth 54 with respect to the first locking teeth 52 to facilitate movement of the first and second locking teeth into intermeshed relation. With the first and second locking teeth 52 and 54 so engaged, such as illustrated in FIG. 6, the clamping force which is created between first clamping surfaces 38 and/or second clamping surfaces 40 is maintained. By providing a plurality of the first locking teeth 52 each of which is engagable by at least one of the second locking teeth 54, the inherent resilience of the clamp 30 permits the clamping force exerted to be selectively varied for added versatility.

As previously discussed, disengagement of first and second locking teeth 52 and 54 for release of clamp 30 is effected by relative disengaging movement of handle portions 42, 44 generally transversely of the aforesaid plane which extends through the clamp 30. Each of the first and second locking teeth 52 and 54 is uniquely configured to resist disengaging movement of the handle portions 42, 44. Specifically, each of first locking teeth 52 includes a locking face having an offset portion 58. Similarly, each of second locking teeth 54 includes a locking face having an offset portion 60. The locking faces of the first and second teeth are mutually engagable for maintaining the clamp in its closed position, as shown in FIGS. 3 and 6.

Figure 7:
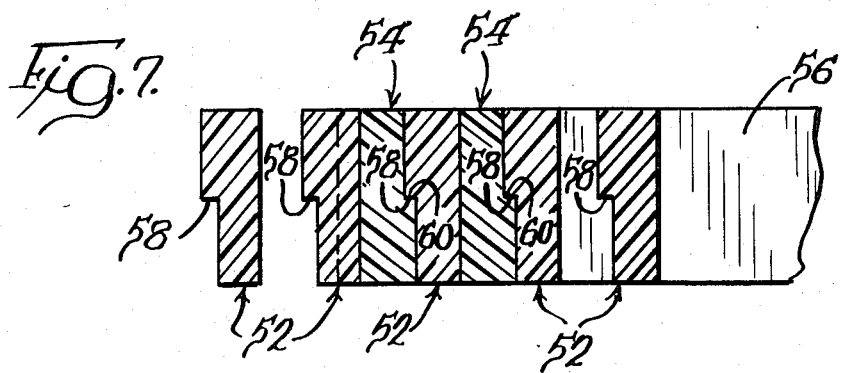
FIG. 7 is a cross-sectional view taken generally along lines 7—7 of FIG. 6.

As best seen in FIG. 7, which shows the two illustrated second locking teeth 54 in respective engagement with two of the first locking teeth 52, the offset portion 60 of each of the second locking teeth 54 is adapted to coact and engage the offset portion 60 of the respective one of the first locking teeth 54. By this coaction, relative disengaging movement of handle portions 42, 44 is resisted in a first direction generally transversely of the plane which extends through the clamp 30. This unique offset or stepped configuration for the locking face of each of the locking teeth acts to resist, but not prevent, relative disengaging movement of handle portions 42, 44 in a direction which urges the offset portions 58, 60 of the respective locking teeth into abutting, confronting relation. When sufficient force is exerted on handle portions 42, 44 to relatively, disengagingly move the handle portions in opposition to offset portions 58 and 60, the offset portions slip out of engagement with each other (due primarily to the flexible resilience of the preferred plastic construction) to permit disengagement of the first and second locking teeth for release of the clamp. As will be recognized, however, the resistance created by the engagement of the respective offset portions 58 and 60 is sufficient to act to preclude inadvertent relative movement of the clamp handle portions in a first of the two directions of relative disengaging movement.

While the intermeshing locking teeth of the clamp 30 could be configured to resist relative disengaging movement of handle portions 42, 44 by providing the respective locking faces of the first and second locking teeth with generally complementary projections and projection-receiving means, considerations of economical manufacture dictate that the first and second locking teeth instead be respectively provided with complementary stepped configurations. Since this illustrated configuration of the locking teeth only resists disengaging movement of the teeth in a first direction, means are preferably provided on the clamp for resisting disengaging movement of the handle portions in a second direction opposite the first direction. To this end, clamp 30 includes coacting abutment surfaces respectively provided on handle portions 42, 44 which are engagable with each other to resist relative disengaging movement of the handle portions in a direction opposite to the direction of relative disengaging movement which is resisted by coaction of offset portions 58, 60 of first and second locking teeth 52 and 54.

In the illustrated embodiment, clamp 30 includes a first abutment projection 62 having an abutment surface 64, and a second abutment projection 66 having an abutment surface 68, with the first and second abutment projections respectively provided on and extending generally inwardly of handle portions 42, 44. As best illustrated in FIG. 4, which is a cross-sectional view of the clamp 30 in its closed condition, the abutment surfaces 64 and 68 are moved into generally confronting, mutually overlapping relation when the finger grips 46, 46 of handle portions 42, 44 are moved toward each other for engaging first and second locking teeth 52 and 54. In this disposition of projections 62 and 66, their respective abutment surfaces 64 and 68 are adapted to coact and engage each other to resist, but not prevent, relative disengaging movement of handle portions 42, 44 in a second direction opposite to the direction of relative movement of the handle portions which is resisted by the coacting offset portions 58 and 60 of first and second locking teeth 52 and 54.

As will be recognized, the provision of coacting abutment surfaces such as 64 and 68 on handle portions 42, 44 for resisting relative disengaging movement of the handle portions can be configured other than illustrated, and may be configured such that coacting abutment surfaces are provided for resisting relative disengaging movement of the handle portions 42, 44 in both directions of relative movement. It should be further noted that while the provision of generally transversely extending stepped or offset first and second locking teeth 52 and 54 is preferred, mutually engagable locking teeth which extend generally vertically (i.e., generally parallel to the plane extending through the clamp) could alternately be employed, such as illustrated in U.S. Pat. No. 2,962,024, to Raymond. When locking teeth of this description are employed in the present clamp construction, the handle portions are generally relatively movable in only one direction for disengaging the teeth. Accordingly, coacting abutment surfaces such as 64 and 68 can be provided in association with the handle portions of the clamp to resist the relative disengaging movement of the handle portions.

From the foregoing, it will be observed that numerous variations and modifications may be effected without departing from the true spirit and scope of the novel concept of the present invention. It will be understood that no limitation with respect to the specific embodiment illustrated herein is intended or should be inferred. It is, of course, intended to cover by the appended claims all such modifications as fall within the scope of the claims.

What is claimed is:

1. A clamp, comprising:
a pair of pincer portions each having a clamping surface at respective ends thereof;
a pair of handle portions each defining grip means adapted for manipulation by hand;
means interconnecting said pincer portions and said handle portions whereby movement of said grip means of said handle portions toward each other moves said clamping surfaces of said pincer portions toward each other for creating a clamping force between said clamping surfaces;
locking means provided on said handle portions, said locking means being adapted to releasably interengage and coact when said grip means of said handle portions are moved toward each other for maintaining said clamping force between said clamping surfaces, said locking means being disengagable by relative disengaging movement of said handle portions; and
means for resisting said relative disengaging movement of said handle portions for resisting disengagement of said locking means after said locking means have been engaged,
said resisting means comprising abutment surfaces respectively provided on said handle portions, said abutment surfaces being engageable with each other when said locking means are engaged for resisting relative disengaging movement of said handle portions,
said locking means on each of said handle portions comprising at least one locking tooth on each of said handle portions, said locking teeth being adapted to releasably interengage for maintaining said clamping force,
said resisting means further comprising offset means on said locking teeth for resisting relative disengaging movement of said handle portions in a first direction when said locking teeth are interengaged, said abutment surfaces being engageable with each other for resisting relative disengaging movement of said handle portions in a second direction generally opposite said first direction.

2. A clamp in accordance with claim 1, wherein each of said locking teeth extends generally transversely of a plane extending through said handle portions, each of said locking teeth including a locking face, said locking faces being mutually engagable when said locking teeth are interengaged,
said offset means comprising an offset portion of the locking face of each of said locking teeth, said offset portions being engagable with each other when said locking teeth are interengaged for resisting relative disengaging movement of said handle portions in said first direction.

3. A clamp in accordance with claim 1, wherein said locking means comprises a plurality of said locking teeth on one of said handle portions, and at least one said locking tooth on the other of said handle portions adapted to selectively releasably interengage each said locking tooth on said one handle portion for selectively varying and maintaining said clamping force.

4. A clamp in accordance with claim 1, wherein said interconnecting means comprises integral hinge means pivotally connecting said pincer portions intermediate the respective ends thereof, integral hinge means pivotally connecting said handle portions intermediate the respective ends thereof, and integral hinge means pivotally connecting one end of each said pincer portion to one end of a respective one of said handle portions.

5. A clamp in accordance with claim 1, wherein each of said clamping surfaces of said pincer portions comprises a first clamping surface thereof, each of said pincer portion further including a second clamping surface disposed between said first clamping surface thereof and said interconnecting means,
said second clamping surfaces having complementary arcuate configurations to facilitate clamping of a tube therebetween.

6. A clamp, comprising:
a pair of pincer portions each having first and second ends, and each having a clamping surface at the first end thereof;

means pivotally connecting said pincer portions to each other intermediate the respective ends thereof, whereby said clamping surfaces are movable toward and away from each other;

a pair of handle portions each defining finger grip means adapted to be manipulated by hand;

means pivotally connecting said handle portions to each other intermediate the ends thereof;

means respectively pivotally connecting the second end of each said pincer portion to an end of a respective one of said handle portions, whereby movement of said finger grip means of said handle portions toward each other correspondingly moves said clamping surfaces toward each other to create a clamping force between said clamping surfaces;

first locking means on one of said handle portions and second locking means on the other of said handle portions, said first and second locking means being adapted to coact and engage each other when said finger grip means of said handle portions are moved toward each other in a plane extending through said handle portions for maintaining said clamping force between said clamping surfaces, said first and second locking means being disengagable by relative disengaging movement of said handle portions transversely of said plane; and means for resisting said relative disengaging movement of said handle portions for resisting disengagement of said first and second locking means after said first and second locking means have been engaged with each other, said first locking means comprising at least one first locking tooth, and said second locking means comprising at least one second locking tooth adapted to releasably engage said first locking tooth for maintaining said clamping force, said resisting means comprising an offset means forming a part of each of said locking teeth adapted to coact when said teeth are engaged for resisting relative disengaging movement of said handle portions in a first direction.

7. A clamp in accordance with claim 6, wherein said resisting means further comprises a pair of abutment projections respectively provided on said handle portions and each including an abutment surface, said abutment surfaces being engagable with each other when said first and second locking means are engaged with each other for resisting relative disengaging movement of said handle portions in a second direction generally opposite said first direction.

8. A clamp in accordance with claim 7, wherein said first locking means comprises a plurality of said first locking teeth each releasably engagable by said second locking tooth whereby the clamping force created between said clamping surfaces can be selectively varied.

9. A clamp in accordance with claim 6, wherein said clamp is of one-piece, unitary plastic construction, each of said pivotally connecting means comprising living hinge means.

10. A clamp in accordance with claim 6, wherein each said clamping surface of said pincer portions comprises a first clamping surface thereof, each said pincer portion further including a second clamping surface disposed intermediate said first clamping surface thereof and said means pivotally connecting said pincer portions, said second clamping surfaces having complementary arcuate configurations.

11. A unitary, one-piece plastic clamp, comprising:

a pair of pincer portions each having first and second ends, and each having a first clamping surface at the first end thereof;

living hinge means pivotally connecting said pincer portions to each other intermediate the respective ends thereof, whereby said clamping surfaces are movable toward and away from each other in a plane extending through said pincer portions;

a pair of handle portions through which said plane extends each defining a respective finger grip adapted to be manipulated by hand;

living hinge means pivotally connecting said handle portions to each other intermediate the respective ends thereof;

living hinge means respectively pivotally connecting the second end of each said pincer portion to an end of a respective one of said handle portions, whereby movement of the finger grips of the handle portions toward each other in said plane moves the clamping surfaces of said pincer portions toward each other to create a clamping force between the clamping surfaces;

first locking means on one of said handle portions comprising at least one first locking tooth, and second locking means on the other of said handle portions comprising at least one second locking tooth adapted to releasably engage and coact with said first locking tooth for maintaining said clamping force between said clamping surfaces, said first and second locking teeth being disengagable by relative disengaging movement of said handle portions generally transversely of said plane; and means for resisting said relative disengaging movement of said handle portions for resisting disengagement of said first and second locking teeth, said resisting means comprising an offset portion forming a part of each of said locking teeth, said offset portions of said first and second locking teeth being adapted to coact and engage each other when said first and second locking teeth are engaged for resisting relative disengaging movement of said handle portions in a first direction with respect to said plane, said resisting means further including a pair of abutment projections each having an abutment surface respectively provided on said handle portions, said abutment surfaces being positioned in generally confronting relation when said first and second locking teeth are engaged whereby said abutment surfaces are engagable with each other to resist relative disengaging movement of said handle portions in a second direction generally opposite said first direction.

12. A one-piece plastic clamp in accordance with claim 11, wherein each of said clamping surfaces comprises a first clamping surface of the respective one of said pincer portions, each said pincer portion further including a second clamping surface disposed between the first clamping surface thereof and said hinge means pivotally connecting said pincer portions, said second clamping surfaces having complementary arcuate configurations to facilitate clamping of a tube therebetween, said first locking means comprising a plurality of said first locking teeth each engagable by said second locking tooth for selectively varying the clamping force between said first and second clamping surfaces.

* * * * *